United States Patent [19]
Fost et al.

[11] Patent Number: 5,849,313
[45] Date of Patent: Dec. 15, 1998

[54] SILICONE MODIFIED PHOSPHOLIPID COMPOSITIONS

[75] Inventors: Dennis L. Fost, Ridgewood; Abe Berger, Summit, both of N.J.

[73] Assignee: Mona Industries, Inc., Paterson, N.J.

[21] Appl. No.: 835,321

[22] Filed: Apr. 7, 1997

Related U.S. Application Data

[63] Continuation-in-part of Ser. No. 420,748, Apr. 12, 1995, Pat. No. 5,623,043.

[51] Int. Cl.$^6$ .............................. A61K 7/00; C08G 77/04; C07F 7/10
[52] U.S. Cl. .............................. 424/401; 424/59; 424/64; 424/65; 424/70.1; 424/70.11; 424/76.1; 514/844; 514/880; 528/26; 528/26.5; 528/27; 528/28; 528/38; 556/400; 556/405; 548/406
[58] Field of Search .............................. 424/401, 59, 64, 424/65, 70.1, 70.11, 76.1, DIG. 1, DIG. 2, DIG. 5; 514/63, 103, 172, 844, 880, 881; 528/26, 26.5, 27, 28, 38; 556/400, 405; 548/406

[56] References Cited

U.S. PATENT DOCUMENTS 5,237,035  8/1993  O'Lenick ................................. 528/27

*Primary Examiner*—Gollamudi S. Kishore
*Attorney, Agent, or Firm*—Franklyn Schoenberg; Norman E. Lehrer

[57] ABSTRACT

A silicone-containing phospholipid having the general formula:

$$R_9-Y-O-\overset{O}{\underset{A_1}{\overset{\|}{P}}}-O-\left[\overset{O}{\underset{OA}{\overset{\|}{P}}}-O\right]_x-A$$

wherein:
A is selected from H, M or $R_9$—Y—;
$A_1$ is selected from H, OH, OM or $R_9$—Y—O—;
M is a cation;
Y is alkylene;
x is 0 or an integer from 1–5; and
$R_9$ is a mixture of a organosilicone carboxyl functional moiety of the formula:

$$\left[R_{10}-(CH_2)_n-F_{n1}-B_{n2}-F-N\underset{O}{\overset{\overset{O}{\|}}{\underset{}{\bigg\langle\!\!\!\bigg\langle}}}\overset{C}{\underset{}{-}}O\right]_d-$$

wherein:
$R_{10}$ is the silicone backbone chain to which at least one pyrrolidone containing carboxyl functional group is attached;
F is linear or branched alkylene of 1–12 carbon atoms;
$X^-$ is an anion;
n is 0 or 2;
$n^1$ is 0 or 1;
$n^2$ is 0 or 1;
B is —$NR_{11}$ sulfur or oxygen, wherein R11 hydrogen or lower alkyl ($C_{1-6}$); and
d is one or greater;
an organic amidoamine moiety and/or an organic tertiary amine moiety.

16 Claims, No Drawings

SILICONE MODIFIED PHOSPHOLIPID COMPOSITIONS

RELATED APPLICATIONS

This application is a continuation in part of application Ser. No. 420,748 filed Apr. 12, 1995 now U.S. Pat. No. 5,623,043.

FIELD OF THE INVENTION

The present invention relates to novel organosilicone compositions and, more particularly, to silicone compositions having a carboxyl functional group thereon and to derivatives thereof having at least one esterified phosphate group in the molecule.

BACKGROUND OF THE INVENTION

Phosphate esters, quaternary ammonium compounds, betaines and certain substituted betaines are known in the art and have been commercially used over the years for a variety of applications, including those requiring surfactant properties. More recently, various betaine derivatives having, in general, specific quaternary compounds linked to phosphate esters referred to as phosphobetaines, and more particularly "synthetic phospholipids," have been disclosed, for example, in U.S. Pat. Nos. 4,215,064, 4,233,192 and 4,380,637 to Lindemann et al.; U.S. Pat. Nos. 4,209,449, 4,336,385 and 4,503,002 to Mayhew et al.; U.S. Pat. Nos. 4,243,602, 4,283,542 and 4,336,386 to O'Lenick et al; and U.S. Pat. No. 4,617,404 to Lukenbach et al. These synthetic phospholipids are disclosed as exhibiting outstanding foaming, viscosity building, wetting, cleansing, detergency, anti-static, conditioning and emulsifying properties, making them useful in industrial applications calling for high performance surface active agents. The synthetic phospholipids are also described as being highly stable compounds which are well tolerated by human tissue (i.e. they exhibit exceptionally low oral toxicity and ocular irritation) and, hence, are well suited for use in a variety of personal care applications including cosmetic formulations as well as in industrial processes.

A variety of organosiloxane compositions including compositions which exhibit excellent properties as surface active agents, lubricants and the like are known and have been used commercially over the years for many different applications, including personal care and home care products. In general, however, organosiloxane compositions are water insoluble, which has limited their use for many applications. Recently, particular types of betaine and phosphobetaine modified organosiloxanes having improved, although limited water solubility properties have been disclosed, for example, in U.S. Pat. Nos. 4,609,750 and 4,654,161 to Kollmeier et al. and U.S. Pat. No. 5,091,493 to O'Lenick et al. Such compositions are suggested as exhibiting high foaming characteristics in water, substantivity to a variety of surfaces and reduced irritation to the eyes and skin. While, as indicated, certain organosilicone containing phosphobetaine compositions and methods for preparing the same heretofore have been suggested, there has been no disclosure or suggestion of the novel silicone-containing phospholipid compositions described in copending application Ser. No. 420,748 of which the present applications is a continuation in part, and in the present application, which compositions exhibit a wide range of properties including improved solubility in a variety of solvents including water.

SUMMARY OF THE INVENTION

It is accordingly an object of the present invention to provide novel silicone-containing compositions which exhibit improved solubility characteristics particularly improved aqueous solubility.

It is another object of the present invention to provide novel silicone-containing phospholipid compositions which exhibit excellent surface-active properties including high foaming, are well tolerated by human tissue, are substantive to the surface of a variety of substrates such as fiber, and the like.

It is a further object of the present invention to provide novel soluble, preferably water soluble silicone-containing phospholipid compositions having functional phophorous containing groups linked terminally, laterally, or combination(s) of terminal and lateral linkages to the polysiloxane, and to a method for preparing such compositions with a variety of concentrations of silicone, as desired or required.

It is still another object of the present invention to provide improved cosmetic and personal care preparations which include novel soluble, preferably water soluble, silicone-containing phospholipid compositions compatible with a variety of surfactant compositions and particularly compositions and methods for treating hair and for skin treatment.

It is yet another object of the present invention to provide improved preparations useful in the manufacture and treatment of paper and textile products which include novel soluble, preferably water soluble, silicone-containing phospholipid compositions compatible with a variety of surfactant compositions.

In accordance with the present invention, there has now been discovered novel silicone containing phospholipid compositions that may be represented by the following general formula:

$$R_9-Y-O-\underset{\underset{A_1}{|}}{\overset{\overset{O}{\|}}{P}}-O-\left[\underset{\underset{OA}{|}}{\overset{\overset{O}{\|}}{P}}-O\right]_x-A$$

wherein:
A is selected from H, M and $R_9$—Y—;
$A_1$ is selected from H, OH, OM and $R_9$—Y—O—;
M is a cation, preferably an alkali metal;
x is 0 or an integer from 1 to 5;
Y is alkylene or substituted alkylene; and
$R_9$ is a silicone-containing moiety of the formula a) and the mixture thereof with an organic amidoamine moiety of the formula b) or organic tertiary amine moiety of the formula c) or mixtures of formula b) and formula c)

a) an organosilicone moiety of the formula:

$$\left[R_{10}-(CH_2)_n-F_{n1}-B-F_{n2}-F-N\begin{array}{c}\diagup\\\diagdown\end{array}\begin{array}{c}\overset{O}{\overset{\|}{C}}\diagdown_O-\\\diagup\\O\end{array}\right]_d$$

wherein:
$R_{10}$ is a silicone backbone chain to which a pyrrolidone-containing oxycarbonyl functional group as hereinafter described can be attached.
F, which can be the same or different, is linear or branched alkylene of 1–12 carbon atoms;
n is 0 or 2;
$n^1$ is 0 or 1;

$n^1$ is 0 or 1;

B is —$NR_{11}$, sulfur (S) or oxygen (O) wherein $R_{11}$ is hydrogen or lower alkyl (C1–6); with the proviso that when n is 0 and $n_2$ is 1, $n_1$ is 1, when n is 2 and $n_2$ is 1, $n_2$ is 1, $n_1$ is 0 or 1 and when n is 2 and $n_2$ is 0, $n_1$ is 0; and d is one or greater, preferably 2–10;

b) a quaternized organic amidoamine moiety of the formula:

$$\left[ R_{12}\overset{O}{\underset{\|}{C}} \left[ N(CH_2)_{n4} \overset{R_6}{\underset{|}{\phantom{N}}} \overset{O}{\underset{\|}{C}} \right]_g \overset{R_4}{\underset{|}{N}} (CH_2)_{n3} \overset{R_7}{\underset{R_8}{\underset{|}{N^*}}} \right] X^-$$

wherein:

$R_{12}$ is alkyl, alkenyl, alkoxy or hydroxyalkyl of from 5 to 21 carbon atoms each, alkaryl or aryl of up to 20 carbon atoms;

$R_6$ is hydrogen or alkyl, hydroxyalkyl or alkenyl of up to 6 carbon atoms, cycloalkyl of up to 6 carbon atoms, or polyoxyalkylene of up to 10 carbon atoms, preferably of from 2 to 5 carbon atoms, within the oxyalkylene unit;

$R_7$ and $R_8$ which may be the same or different, are selected from alkyl, hydroxyalkyl, carboxyalkyl of up to 6 carbon atoms in each alkyl moiety, and polyoxyalkylene of up to 10 carbon atoms; in addition $R_7$ and $R_8$ taken together with the nitrogen to which they are attached may represent an N-heterocycle;

$X^-$ is an anion, preferably a halogen;

g is 0 or 1;

$n^3$ is integer from 2 to 12; and $n^4$ is 1 or greater; and c) an organic quaternized tertiary amine moiety of the formula:

$$\left[ R_{13}\overset{R_{14}}{\underset{R_{15}}{\underset{|}{\overset{|}{N^+}}}} \right] X^-$$

wherein:

$R_{13}$, $R_{14}$ and $R_{15}$ are the same or different and are alkyl, substituted alkyl, alkyl aryl or alkenyl groups of up to 16 carbon atoms with the proviso that the total carbon atoms in $R_{13}+R_{14}+R_{15}$ is between 10 and 24; with the proviso that at least 5 equivalent weight percent and preferably to about 80 equivalent weight percent of the the total equivalent weight of the organosiloxane and the phospholipid composition is an organosilicone moiety.

It is evident from the general phospholipid formulae above that the functional phosphorus containing group(s) can be linked terminally, laterally or both terminally and laterally to the polysiloxane chain through the carbofunctional, amidoamine and/or tertiary amine functional group.

In another aspect of the present invention there is provided cosmetic and personal care compositions comprising from about 0.1% to about 10%, preferably from about 1%, soluble, and preferably water soluble, silicone-containing phospholipid compositions selected from the group consisting of phospholipid compositions that may be represented by the general formula:

$$R_9-Y-O-\overset{O}{\underset{\underset{A_1}{|}}{\overset{\|}{P}}}-O-\left[\overset{O}{\underset{\underset{OA}{|}}{\overset{\|}{P}}}-O\right]_x-A$$

Wherein A, $A_1$, and $R_9$ are as defined above.

DESCRIPTION OF THE PREFERRED EMBODIMENT

In accordance with the present invention, there are provided novel phospholipid compositions including high molecular weight polysiloxanes which comprise a class of silicone-containing phospholipid compositions which exhibit a surprising and unexpected solubility in aqueous systems and/or aqueous/co-solvent systems. Such novel silicone-containing phospholipid compositions may be represented by the general formula:

$$R_9-Y-O-\overset{O}{\underset{\underset{A_1}{|}}{\overset{\|}{P}}}-O-\left[\overset{O}{\underset{\underset{OA}{|}}{\overset{\|}{P}}}-O\right]_x-A$$

wherein:

A is selected from H, M and $R_9$—Y—;

$A_1$ is selected from H, OH, OM and $R_9$—Y—O

M is a cation, preferably an alkali metal;

x is 0 or an integer from 1 to 5;

Y may be alkylene optionally interrupted by up to 3 oxygen atoms, of up to 12 carbon atoms which alkylene chain may optionally be substituted with lower alkyl, alkoxyalkyl or hydroxyl, e.g. not more than 10 carbon atoms each; and $R_9$ is a silicone-containing moiety of the formula a) and the mixture thereof with an organic amidoamine moiety of the formula b) or tertiary amine moiety of the formula c) or mixtures of formula b) and formula c);

a) an organosilicone moiety of the formula:

$$\left[ R_{10}\!-\!\!\!\left(CH_2\right)_n\!\!F_{n1}\!\!-\!B_{n2}\!\!-\!F\!-\!N \underset{\underset{O}{\|}}{\overset{\overset{O}{\|}}{\diagup\diagdown}} \overset{C}{\underset{O}{\|}}\!\!-\! \right]_d$$

wherein:

$R_{10}$ is a silicone backbone chain to which at least one pyrrolidone containing oxycarbonyl functional group as herein described can be attached;

F, which can be the same or different, is linear or branched alkylene of 1–12 carbon atoms;

n is 0 or 2;

$n^1$ is 0 or 1;

$n^2$ is 0 or 1;

B is —$NR_{11}$, sulfur (S) or oxygen (O) wherein $R_{11}$ is hydrogen or lower alkyl (C1–6); with the proviso that when n is 0 and $n_2$ is 1, $n_1$ is 1, when n is 2 and $n_2$ is 1, $n_2$ is 1, $n_1$ is 0 or 1 and when n is 2 and $n_2$ is 0, $n_1$ is 0; and d is one or greater, preferably 2–10;

b) a quaternized organic amidoamine moiety of the formula:

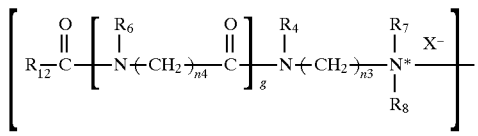

wherein:
R$_{12}$ is alkyl, alkenyl, alkoxy or hydroxyalkyl of from 5 to 21 carbon atoms each, alkaryl or aryl of up to 20 carbon atoms;
R$_6$ is hydrogen or alkyl, hydroxyalkyl or alkenyl of up to 6 carbon atoms each, cycloalkyl of up to 6 carbon atoms, or polyoxyalkylene of up to 10 carbon atoms, preferably of from 2 to 5 carbon atoms, within the oxyalkylene unit;
R$_7$ and R$_8$ which may be the same or different, are selected from alkyl, hydroxyalkyl, carboxyalkyl of up to 6 carbon atoms in each alkyl moiety, and polyoxyalkylene of up to 10 carbon atoms; in addition R$_7$ and R$_8$ taken together with the nitrogen to which they are attached may represent an N-heterocycle;
X$^-$ is an anion, preferably a halogen; g is 0 or 1;
n$^3$ is an integer from 2 to 12; and
n$^4$ is 1 or greater; and/or
c) an organic quaternized tertiary amine moiety of the formula:

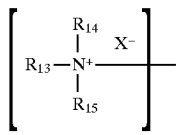

wherein:
R$_{13}$, R$_{14}$ and R$_{15}$ are the same or different and are alkyl, substituted alkyl, alkyl aryl or alkenyl groups of up to 16 carbon atoms with the proviso that the total carbon atoms in R$_{13}$+R$_{14}$+R$_{15}$ is between 10 and 24;
X$^-$ is an anion, preferably a halogen;
with the proviso that at least 5 equivalent weight percent and preferably to about 80 equivalent weight percent of the total equivalent weight of organosiloxane and amine moieties of the phospholipid composition is a organosilicone moiety.

Preferred silicone-containing phospholipid compositions of the invention wherein Y is 2-hydroxypropylene comprise a class of compositions which may be represented by the general formula;

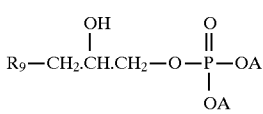

wherein
A and R$_9$ are as defined above.

The silicone backbone chain R$_{10}$ to which the pyrrolidone containing carboxyl functional group hereinabove shown (represented below as R$_1$) are attached corresponds to the general formula:

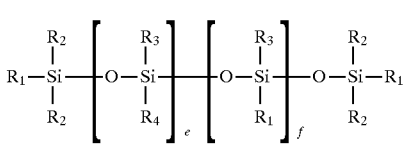

wherein:
R$_1$, which can be the same or different, can be selected from R$_2$, a primary amine containing group and a pyrrolidone containing group of the formula:

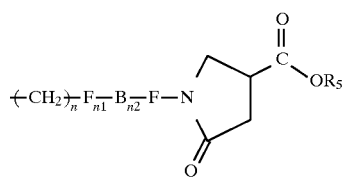

wherein at least one of R$_1$ is a pyrrolidone containing carboxyl functional group as shown; F, which can be the same or different is a linear or branched alkylene of 1–12 carbon atoms; R$_2$ is as defined below; R$_5$ is selected from hydrogen or alkyl of up to 10 carbon atoms; n is 0 or 2; n$^1$ is 0 or 1; n$^2$ is 0 or 1; n$^3$ is an integer from 2 to 12; and B is —NR$_{11}$, sulfur (S) or oxygen (O), wherein R$_{11}$ is hydrogen or alkyl, preferably lower alkyl (C$_{1-6}$); with the proviso that when n is 0 and n$^2$ is 1, n$^1$ is 1, when n is 2 and n$^2$ is 1, n$^1$ is 0 or 1, and when n is 2 and n$^2$ is 0, n$^1$ is 0;
R$_2$ can be the same or different and can be selected from alkyl, aryl, alkenyl or alkynyl;
R$_3$ and R$_4$, which may be the same or different, are selected from alkyl, aryl, capped or uncapped polyoxyalkylene, alkaryl, aralkylene and alkenyl (vinyl);
e can be an integer from 0 to 100,000; and
f can be an integer from 0 to 1000.

It is evident from the general formulae of the novel phospholipid compositions of the invention that the functional phosphorus containing group(s) can be linked terminally, laterally or both terminally and laterally to the siloxane chain through the pyrrolidone-containing carboxyl functional group containing alkylene groups which can contain heteroatom atoms.

In accordance with the invention, the phospholipid compositions of the invention can be prepared by reacting combinations of carboxyl functional, organosiloxne organic amidoamine and/or tertiary amine reactants with phosphate, polyphosphate or phosphite ester halide reactants in appropriate stoichiometric quantities as will be described in detail hereinafter to obtain the desired products of the formulae:

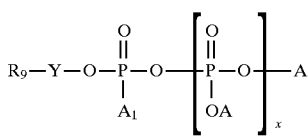

and preferably

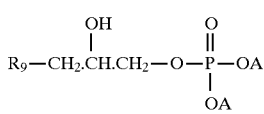

wherein:
A is as defined hereinabove;
A$_1$ is as defined hereinabove;
Y is as defined hereinabove;
x is as defined hereinabove;
M is as defined hereinabove; and
R$_9$ is a mixture of moieties selected from the group consisting of a pyrrolidone containing oxycarbonyl functional organosilicone moiety, quaternized organic amidoamine and/or organic quaternized tertiary amine moiety as defined hereinabove;
with the proviso that at least 5 equivalent weight percent to about 80 equivalent weight percent of the total equivalent weight of organosiloxane and amine moieties of the phospholipid composition is an organosilicone moiety.

The intermediate reactants required in the processes for preparing the silicone-modified phospholipid compounds of the invention can be prepared as described hereinafter.

Phosphate, polyphosphate and/or phosphite ester intermediate reactants suitable for use can be prepared by known procedures illustrated as follows:

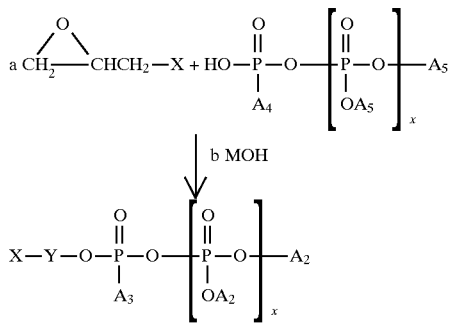

wherein:
$A_2$ is selected from H, M and X—Y—;
$A_3$ is selected from H, OH, OM and X—Y—O—;
$A_4$ is H, OM or OH;
$A_5$ is H or M;
a is from 0.5 to 3.5. preferably 1 to 3;
b is from 1 to 3; preferably 1 to 2;
M is a cation, preferably an alkali metal;
x is 0 or an integer from 1 to 5;
X is halogen; and
Y is 2-hydroxypropylene.

The above coupling reaction (I) is carried out in an aqueous media, preferably in the range of 30–50% concentration, having a pH range of 5.0–8.0.

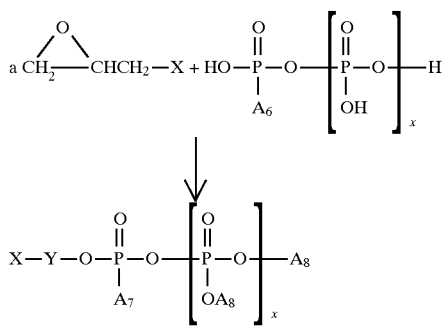

wherein:
$A_6$ is selected from H or OH;
$A_7$ is selected from H, OH or X—Y—O—;
$A_8$ is H or —Y—X;
a is from 0.5 to 7, preferably from about 1 to 3;
x is 0 or an integer from 1 to 5;
X is halogen; and
Y is 2-hydroxypropylene.

The above reaction (II) is preferably carried out in the absence of water.

Phosphate, phosphite and polyphosphate ester halide intermediate reactants for preparing phosphobetaine, pyrophospobetaine and the like compositions of the invention can also be prepared by known procedures such as disclosed, for example, in U.S. Pat. No. 4,617,414.

Also suitable as phosphate and phosphite intermediate halide reactants are such reactants prepared by known procedures illustrated as follows:

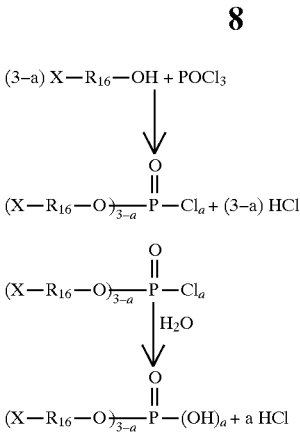

wherein:
a is 0 or an integer from 1 to 2;
X is halogen; preferably bromine; and
$R_{16}$ is alkylene.

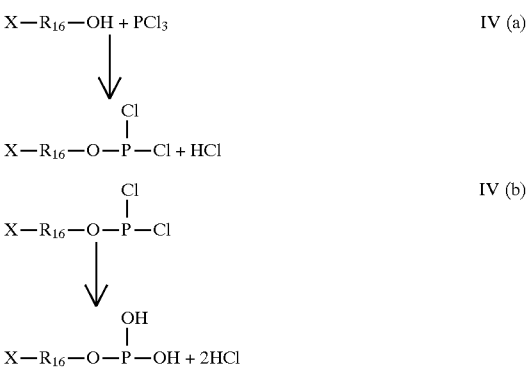

wherein:
X is a halogen; preferably bromine; and
$R_{16}$ is alkylene.

Carrying out reactions III(a) and IV(b) in the presence of a tertiary amine HCl acceptor is preferred to prevent any secondary reaction with the generated HCl gas.

The carboxyl functional polysiloxanes or derivatives thereof (terminal, lateral or combinations of terminal and lateral) applicable for use as intermediate reactants in accordance with the practice of the invention can be prepared by procedures such as disclosed in U.S. Pat. No. 5,596,061. Such procedures include the reaction of corresponding silicone compositions or fluids having one or more functional primary amine groups including diamine groups containing functional primary amine groups with up to about one equivalent, preferably about stoichiometric quantities, of itaconic acid or its ester per functional amine group at an elevated temperature for the time sufficient for substantially all of the itaconic acid or its ester to react with the functional primary amine group(s). In general, from about at least 0.5 preferably, from about 0.9 to about 1.1 equivalents of itaconic acid or its ester per functional primary amine group is reacted with the silicone fluid wherein substantially all itaconic acid is reacted with the functional primary amine group(s) and polysiloxane compositions with at least one pyrrolidone containing functional carboxyl group(s) and/or its ester are formed.

The reaction can be carried out neat or in an inert solvent such as alcohol, hydrocarbon solvent, chlorinated hydrocarbon and the like, in general, at elevated temperature, preferably from about 90° C. to about 130° C. The reaction readily proceeds and generally complete reaction of the itaconic acid or its ester with the available functional primary amine groups and cyclization to form the pyrrolidone group will occur in from about 1 to 5 hours, with routine analytical techniques for amine and acid values as well as monitoring water and/or alcohol evolution being used to determine completion of the reaction.

Amine functional silicone fluids suitable for use in preparing the carboxyl-functional silicone fluids having one or more primary amine functional group(s) including diamine groups that contain primary amine groups, which may be linked terminally, laterally or both terminally and laterally, are well known and are available commercially, for example, from Dow Corning, Th. Goldschmidt AG and Shin-Etsu. The equivalent weight of the silicone fluids or compositions which may be employed in the preparation of the pyrrolidone containing carboxyl functional polysiloxanes is not critical, and suitable compositions may have amine functional fluid equivalent weights of 5,000 to 10,000 or even higher, but silicone fluids having equivalent weights from about 500 to about 5,000 are in general preferred.

As indicated, the carboxyl-functional polysiloxanes compositions are readily prepared by reaction of amine functional silicone fluids containing primary amine groups with itaconic acid or its ester. Itaconic acid (methylene succinic acid) is a compound of the formula:

$CH_2=C\ (COOR_{11})\ CH_2\ COOR_{11}$ wherein:
$R_{11}$, which can be the same or different is hydrogen or lower alkyl ($C_{1-6}$).

The compound is available commercially from Rhone Poulanc and Pfizer Chemicals Division and ester derivatives thereof are available from Norflex, Inc., Greensboro, N.C. The compound is produced by known fermentation techniques although chemical synthesis methods are also known.

As noted above, silicone-containing phospholipid compositions of the invention can be prepared by reacting the combination of desired carboxyl functional silicone, organic amidoamine and/or tertiary amine reactants with phosphate, phosphite and/or polyphosphate ester halide reactants in appropriate stoichiometric proportions, in general, in molar equivalents of from about 0.7 to 3.3 of the combination of carboxyl functional silicone and organic amine reactants to 1 of the phosphate ester halide reactant. Such reaction can be carried out in a water solution or in conjunction with a co-solvent such as isopropyl alcohol, ethylene glycol, propylene glycol, ethyl cellosolve or the like. The reaction is carried out generally at elevated temperatures up to about 100° C., preferably from about 75° to 95° C., for a time ranging from about 1 to 5 hours, and generally until the amine reactants are substantially completely reacted. The course of the reaction can be determined by alkali number titration, ionic chloride determination, etc.

The reaction of the mixture of carboxyl functional silicone, organic amidoamine and/or organic tertiary amine reactants and phosphate, phosphite and/or polyphosphate ester halide reactants can be readily carried out in an aqueous or an aqueous/organic co-solvent reaction system. Surprisingly and unexpectedly, it has been found that the phospholipid compositions of the invention can be prepared in substantially completely soluble reaction systems using carboxyl functional silicone reactants as herein described having equivalent weights 5,000 to about 10,000, or even greater, by incorporating in the reaction system organic tertiary amine and/or preferably organic amidoamine reactants as herein described, in conjunction with the carboxyl functional silicone reactants. Suitable organic tertiary amine and/or amidoamine-containing reactants are added to the reaction system as a partial replacement of a substantially molar equivalent amount of the carboxyl functional silicone reactant, thus substantially maintaining the above noted molar equivalent ratios of organosiloxane and amine reactants to phosphate ester halide reactants in the reaction mixture.

Organic amidoamine intermediate reactants suitable for use in preparing the phospholipid compositions of the invention can be prepared as follows:

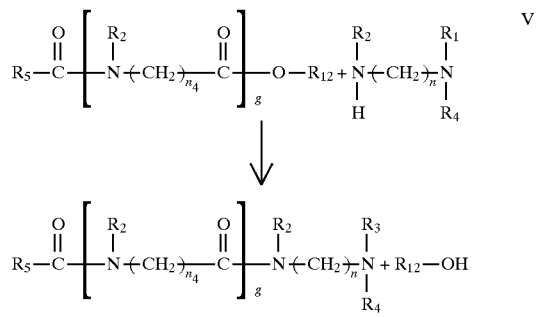

wherein:
$R_{12}$ is alkyl, alkenyl, alkoxy or hydroxyalkyl of from 5 to 21 carbon atoms each alkaryl or aryl up to 20 carbon atoms;
$R_6$ is hydrogen or alkyl, hydroxyalkyl or alkenyl of up to 6 carbon atoms, cycloalkyl of up to 6 carbon atoms, or polyoxalkylene of up to 10 carbon atoms, preferably of from 2 to 5 carbon atoms, within the oxyalkylene unit;
$R_7$ and $R_8$ is as hereinabove defined;
$R_5$ is hydrogen or alkyl;
g is 0 or 1;
$n^3$ is an integer from 2 to 12; and
$n^4$ is 1 or greater.

The organic amidoamines suitable for use as intermediate reactants in preparing the phospholipid compositions are known and are generally prepared using conventional techniques such as shown in the above coupling reaction (V). A variety of suitable organic amidoamines are commercially available as well as are tertiary amino alkyl amines which are suitable for reaction with an acid or acid derivative to prepare suitable amidoamines. Suitable tertiary amino alkyl amines can be primary or secondary amines with the proviso that the total number of carbons in the acid portion of the molecule is greater than 6, i.e. to give a hydrophobic moiety necessary for surface activity properties. Suitable organic amidoamines may also be derived from acyl derivatives of aminoacid products such as glycine and sarcosine (N-methylglycine) including, for example, products available under the Tradename HAMPOSYL from the Hampshire Chemical Co.

Organic tertiary amine reactants suitable for use in preparing the phospholipid compositions of the invention can be prepared using procedures well known in the art and many suitable compositions are available.

Exemplary tertiary amines include:
tributylamine
bis(hydroxyethyl)hexylamine
bis(2-hydroxyethyl)cocoamine
N,N-dimethyl-dodecylamine
N,N-dimethyl-tetradecylamine
N,N-dimethyl-hexadecylamine
N, N-dimethyl-cocoamine
N,N-dimethyl-cetylamine
dimethyl ($C_8$–$C_{16}$) alkyl amine N,N-dimethyl-octadecylamine In accordance with the method of the invention, the order of addition of the reactants in preparing the phospholipid compositions of the invention is not critical although it may be advantageous for certain applications to add an excess amount of N-acylated amidoamine reactant derived from an amino acid after all the other ingredients have been added. While a heterogeneous mixture may result when all reactants are initially admixed, the reaction system becomes homogeneous as the reaction proceeds. The reaction may start slowly while the mixture is heterogeneous but the reaction mixture will become substantially clear as the reaction proceeds. In accordance with the process of the invention, silicone-containing phospholipid compositions which contain at least 5 weight percent to about 80 weight percent of the organosiloxane portion of the total solids of the reaction product can be prepared, which silicone-containing phospholipid compositions will be completely dispersible or soluble in an aqueous/solvent medium or, preferably, aqueous systems, while exhibiting surface active properties including low surface tension, high foaming and substantivity characteristics, low ocular and skin irritation and the like. Thus, it is possible by the combination of particular carboxyl functional silicone reactants with organic amidoamine or tertiary amine reactants or mixtures of the same and phosphate ester halide reactants to obtain dispersible or soluble, preferably, aqueous dispersible or soluble silicone-containing phospholipid compositions which exhibit a wide range of beneficial properties suitable for use in a variety of applications.

The novel silicone-containing phospholipid compositions of the invention display many of the well known properties of silicones such as emolliency, emulsification, detackification, smoothing and surfactancy properties while, in addition, exhibiting the unique property of water-dispersibility or solubility and substantivity, thus making them easy to formulate into water-based systems and permitting them to provide long-lasting effects on various substrates such as skin, hair, natural and synthetic fibers (textiles), plastics, paper and the like. Moreover, the novel phospholipid compositions are non-irritating to the eyes and skin, are compatible with other surfactants as well as exhibiting a variety of other characteristics making them well suited for personal care and home care applications.

It is therefore a further aspect of the invention to use the novel compositions of the invention, for example, in cosmetic preparations and the like, especially in preparations for hair care and skin treatment. In this connection, personal care formulations can be shampoos, hair conditioners, skin treatment cremes and lotions and after bath skin moisturizers, depending on whether the emphasis is on the cleansing effect or on the conditioning effect including the effect on better combability in hair care products. Other formulations where the unique properties of the novel compositions of the invention can be utilized include make-up cremes, sunscreens, lipstick, pressed powders, skin-toners, deodorants, antiperspirants and the like. Shampoos to which the novel phospholipid compositions of the invention have been added in amounts of 0.1 to 10 weight percent, and which contain up to about 30 weight percent of substances with detergent activity, besides water and possibly other additives cause washed hair to have fullness and an agreeable hand, to show a desirable gloss and to be easily combable. Practically no electrostatic charging of the hair is observed. In hair care products, such as, hair tonics or hair sprays, the composition of the invention in amounts of 0.1 to 5% by weight already bring about a significant improvement in combability of the hair as well as development of fullness and gloss.

Conventional additives, such as thickeners, perfumes, preservatives, complexing agents, foam stabilizers, opacifiers, luster development agents and the like may be added to the hair care products.

The novel phospholipid compositions may also be added to skin treating products. As a component of soap or skin cremes, they form a fine non-irritating, non-greasy film on the skin which does not evaporate and therefore provides long lasting protection. In addition, these novel phospholipid compositions also demonstrate useful emulsifying properties, including the unique capability of serving as emulsifying and even as solubilizing agents for a wide range of polysiloxanes.

Among other advantages of the novel phospholipid compositions of the invention are their usefulness as paper and textile sizing and lubricating agents; treating agents for fillers, paper and plastics; hydrophilic coatings for glass, plastics and minerals; anticorrosion agents for metal products; adhesion promoters for metal primers and paints and emulsification agents and even as solubilizing agent for incorporation of a wide range of generally water insoluble silicone fluids in water based personal care and industrial compositions useful for many applications.

The preparation of specific compositions of the invention is illustrated by the following specific examples which are provided herein for purposes of illustration only and are not intended to limit the scope therein.

EXAMPLE 1

An alpha-omega bis primary amino alkyl dialkyl functional polysiloxane fluid obtained commercially under the designation Tegomer A-Si2120 from Goldschmidt Company is used in this example. The amine content of the fluid is 3.5% which corresponds to a molecular weight of 914.

91.4 grams of the above polysiloxane fluid (0.1 moles) is admixed with 26 grams (0.2 moles) of Itaconic Acid in a reaction vessel. Upon combination of the reactants, a heterogeneous mixture is formed. External heat is applied to the reaction vessel bringing the reaction mixture to a temperature of about 110° C., whereupon the reaction mixture becomes completely homogeneous while the temperature rises to 140° C.

After a heating period of 4 hours, a total of 7 ½ ml. of volatiles are collected. The acid value of the reaction mixture is 81.6 (theoretical 95.5) which corresponds to a mole weight of 1375 while the alkali number is nil, thus confirming that there is the presence of carboxyl groups on the product.

EXAMPLE 2

An alpha, omega-Bis primary amino alkyl dimethyl polysiloxane fluid with an average molecular weight about 1579.5 and having the general formula:

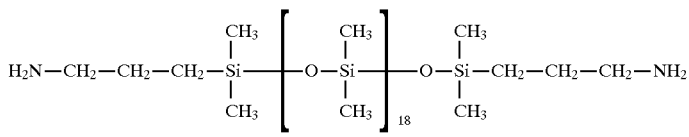

obtained commercially from Shin-Etsu under the designation X-22161A is used in this example.

A mixture of 994.5 grams of the above polysiloxane fluid (0.6296 moles) and 163.7 grams (1.25 moles) of Itaconic Acid is formed in a reaction vessel and heated (slowly to about 90° C. at which point an exotherm occurs raising the reaction vessel temperature to 130° C. and water starts to evolve.

The reaction mixture is heated to and maintained at a temperature of 140° C. to 150° C. for a period of 3 hours during which time about 20 ml. of water and other volatiles are collected. A clear, yellow viscous liquid is formed having an alkali number of 0 and acid number of 52 which corresponds to a mol.weight of 1934.

EXAMPLE 3

A pendant (lateral) aminofunctional silicone fluid obtained from Shin-Etsu under the product designation KF 865 is used in this example. The silicone fluid has an amine value of 0.2219 percent which corresponds to an amine equivalent weight of 5675.

665.9 grams (0.1173 equiv. wt.) of the silicone fluid and 15.25 grams of Itaconic acid (0.1173 mole) are combined with 150 ml of xylene in a reaction vessel and heated to a temperature of 130°–140° C. under reflux. After heating for 4 to 5 hours under reflux, 2.3 ml of water is removed (theory 2.1). A clear, viscous liquid is formed having an alkali number of 0 and acide number of 9.7 (equivalent weight of 5783).

17.3 grams (0.003 equiv. wt.) of the above carboxyl functional silicone product are combined with 2.8 grams (0.007 moles) of N-(dimethylaminopropyl) linoleamide (molecule weight 404); 3.12 grams (0.0033 moles) of a 40% concentration of a phosphate ester halide reactant prepared by the reaction of 3 moles of epichlorohydrin with one mole of 85% phosphoric acid in the presence of one mole sodium hydroxide and 30 grams of additional water in a reaction vessel. The reactant mixture is heated for 3 hours at a temperature of 90°–95° C. The reaction mixture becomes clear and homogeneous. The silicone content of the reaction product based on the total solids is 64%. The product when added to water produces a great deal of stable foam.

EXAMPLE 4

DiSodium 1, 3 Bis 3 chloro-2 hydroxy propyl pyrophosphate is prepared by charging 446 parts of $Na_4P_2O_7$ $10H_2O$ (1 mole) and 178 parts $H_4P_2O_7$ (1 mole) with 1000 parts deionized water to a reaction vessel and reacting the same with 320 parts epichlorohydrin at 60°–80° C. for 3-4 hours.

81.4 parts (0.2 equivalents) of the above reaction product is combined with a mixture of a pendant trimethylsilyl capped pyrrolidone containing carboxyl functional siloxane having an equivalent weight of 1845 (0.05 equivalent) and 57.6 parts of N- (Dimethylaminopropyl) linoleamide (0.15 equivalents) and then diluted with 480 grams of water to a 30% concentration. After the solution is adjusted to a pH of 8, the reaction mixture is heated to 90°–95° for a period of 4–5 hours at which time a clear solution forms. The reaction is monitored via argentometric estimation for covalent chloride to ionic chloride and the reaction is completed in 5 hours.

The reaction product foams well in water.

EXAMPLE 5

A 3-chloro-2 hydroxypropylester salt of phosphorous acid is prepared by charging 41 grams (0.5 mole) of phosphorus, 409 grams of water and 50 grams of 50% NaOH solution (0.6 mole) to a reaction vessel and warmed to 75° C. 46.25 grams (0.5 mole) of epichlorohydrin is then added and the reaction mixture is heated to 75° C. for 1 ½ hours with stirring.

196 parts of the combined epichlorohydrin-phosphite reaction mixture is admixed with 50% sodium hydroxide solution to achieve a pH of 8 followed by adding the combination of a pendant trimethylsilyl capped pyrrolidone containing carboxyl functional silicone having an equivalent weight of 3500 and 27.3 parts of cocoyl sarcosine amidoamine (0.09 equivalents). The reaction mixture is diluted with water to achieve 25% solids.

The reaction mixture is heated to 90° C. for 2 hours whereupon a clear aqueous solution is formed.

EXAMPLE 6

3-Bromopropyl diacid phosphate $[BrCH_2CH_2CH_2OPO(OH)_2]$ is prepared by reacting 3-Bromopropanol with $POCl_3$ while utilizing one equivalent of triethylamine in a methylene chloride solvent. The Dichloride is isolated and hydrolyzed to the diacid with water. The pH of the product in water is adjusted to 8 followed by the addition of an equivalent amount of a 50:50 combination of an alpha, omega, bistrimethylsilyl capped pyrrolidone-containing carboxylic acid silicone having an equivalent weight of 1845 and a N- (dimethylaminopropyl) derivative of linoleamide. The reaction mixture is adjusted with water to 30% of total solids.

The reaction mixture is heated for 4 hours at 90° C. A clear solution is formed.

EXAMPLE 7

The silicone and phosphate ester reactants of example 3 are used in this example.

A mixture of 23.1 grams (0.004 equivalents) of the silicone carboxylic acid composition of example 3 (equivalent weight 6233) with 6.46 grams of N-(dimethyaminopropyl) linoleamide (molecular weight 404; 0.016 moles) is formed in a reaction vessel. To this mixture, 6.24 grams of the 40% active solution of chlorohydroxylpropyl phosphate of example 3 and 48 grams of water are added to prepare a 25% solution.

The reaction mixture is heated to 85°–90° C. for 4 hours. The reaction mixture goes through various stages from several immiscible phases, to a cloudy milky dispersion and then to a clear hazy phase. The sodium chloride content of the reaction product is 0.83% compared to a theoretical amount of 0.86%.

The reaction product containing 20 mole percent of silicone based on the total silicone and amine requirements, when mixed with water produces a large amount of stable foam.

EXAMPLE 8

A mixture of 37.39 grams (0.006 moles) of the silicone carboxylic acid composition of example 3 and 5.6 grams of the N-(dimethylaminopropyl) linoleamide (mol.weight 404) of example 3 is mixed with 6.24 grams of the 40% active solution of chlorohydroxy propyl phosphate ester reactant of example 3 and an additional 132 grams of water in a reaction vessel to prepare a 25% solution.

The reaction mixture is heated for 4 hours at 90° C. and forms a hazy, single phase reaction product which is soluble in water and foams well.

The product has a sodium chloride content of 0.61% (0.64% theoretical) and a silicone content of 30 mole per cent.

EXAMPLE 9

A reaction mixture of 17.57 grams (0.002 moles) of the silicone carboxylic acid composition of example 3, 2.02 grams (0.005 moles) of the N-(dimethyaminopropyl) linoleamide of example 3, 0.7 grams (0.003 moles) of cocoyl dimethylamine and 3.12 grams of the 40% active solution of chlorohydroxylpropyl phosphate ester reactant of example 3 is charged to a reaction vessel. An additional 47 grams of water is added to the reaction mixture to form a 25% solution. The reaction mixture is heated for 4 hours at 90° C. and a homogeneous solution is formed. The product is soluble in water and forms a stable foam.

EXAMPLE 10

A reaction mixture of 11.57 grams (0.002 moles) of the silicone carboxylic acid composition of example 3 (equivalent weight of 5783), 1.5 grams (0.005 moles) of soyadimethyl amine (equivalent weight of 299) and 1.2 grams (0.003 moles) of the N-(dimethyaminopropyl) linoleamide (equivalent weight of 404) of example 3 is prepared in a reaction vessel. 3.12 grams of the 40% active solution of chlorohydroxylpropyl phosphate ester reactant of example 3 and an additional 32 grams of water are added to the reaction mixture to form a 25% solution.

The reaction mixture is heated for 3 hours at 85°–90° C. and a clear solution is formed. The reaction product is soluble in water and forms of a great deal of stable foam.

EXAMPLE 11

A Skin Care Creme composition is prepared having the following proportion of ingredients. The silicone-containing phospholipid composition of example 7 is used in this example.

| Part | Raw Material | Control A % Active | Test Sample % Active | Control B % Active |
| --- | --- | --- | --- | --- |
| A | Glycerin | 10.0 | 10.0 | 10.0 |
| A | Propylene Glycol Stearate | 5.0 | 5.0 | 5.0 |
| A | Cetyl Alcohol | 2.0 | 2.0 | 2.0 |
| A | Glyceryl Monosteorate | 3.0 | 3.0 | 3.0 |
| A | PEG-20 Glycerol Stearate | 3.5 | — | — |
| B | Silicone Phospho lipid from Ex. 7 | — | 1.5 | — |
| B | Deionized Water | 76.5 | 79.5 | 80.0 |
| | | 100.0 | 100.0 | 100.0 |

Heat Parts A & B individually to 75° C. When hot, add Part B and Part B to Part A with agitation. Cool with mixing to 30° C.

Appearance after 24 hours at room temperature (25° C.):
Control A—A moderate viscosity non-glossy, white creme
Control B—separated into layers
Test Sample—A moderate viscosity glossy white creme
Rubine Substantivity Test on wool exposed to creme and rinsed with warm water:
Control A—Non-substantive
Test Sample—Substantive
TRIALS OF CREME ON SKIN When applied to skin, the test sample (contains phospholipid silicone) has a lighter textured, more easily spreadable consistency than the control, and when dry, after rub-in, it has a smooth, non-greasy emollient texture on the skin. The control A sample has a heavier texture and waxier feel on the skin when dry but was also emollient.

After rinsing the skin with warm water and drying, the test sample creme still exhibites residual emolliency and slip-smoothness while the control sample creme does not; this residual effect appears to be due to the demonstrated substantivity of the silicone-containing phospholipid.

The silicone-containing phospholipid composition exhibits multi-functionality in that it serves as an emulsifier, an auxiliary emollient and it imparts emolliency that is water-resistant (a performance advantage for longer wearing skin care products and sunscreen formulations).

EXAMPLE 12

The silicone-containing phospholipid compositions of examples 7, 9 and 10 are used in this example. Hair treating formulations such as shampoos and conditioners are prepared and evaluated as described below.

The evaluation is carried out as follows:
Procedures:
1. 1% by weight active silicone-containing solutions/dispersions are prepared in deionized water and adjusted with lactic acid to the 4–6 pH range.
2. Hair tresses weighing approximately 2 grams each are thoroughly shampooed, rinsed in water and then rinsed in isopropanol and dried prior to use.
3. The tresses are dipped in 50ml of the 1% active silicone-in-water dispersions, combed through ten times, drained and allowed to air-dry overnight prior to further evaluation.
4. A small R&D expert panel evaluated and ranked the tresses after treatment. A deionized water blank is included in the test as a performance benchmark. Numerical rankings assigned as follows:
0=Poor
1=Fair
2=Good
3=Very Good
4=Excellent
5. Silicone-containing compositions are also evaluated at 1.0% active level in 15% active Sodium Lauryl Sulfate plus 2% active coconut monoethanolamide shampoo with pH adjusted to 4–6 range. After washing in the silicone-containing shampoos, hair samples are thoroughly rinsed in tap water, combed through and allowed to air dry prior to further evaluation.

Hair Tresses Washing in 1% Active Silicone in 15% SLS and 2% CMA Shampoo, Rinsed, Combed, Drained and Dried

| 1% Active Silicone in Shampoo | Shampoo Appearance | Wet Combing | Dry Combing | Total Cumulative Score |
|---|---|---|---|---|
| Example 7 | Clear with only trace of opalescence | 3.5 | 3.5 | 7.0 |
| Example 9 | Uniform, light opalescence | 4.0 | 3.5 | 7.5 |
| Example 10 | Initially uniform light opalescence. On standing some supernatant layering | 4.0 | 4.0 | 8.0 |
| $H_2O$ | Clear | 0 | 0 | 0 |

The example 10 sample exhibits excellent performance in combing characteristics and is slightly superior to the example 9 and example 7 samples, however, it is less soluble in this particular shampoo than the sample of example 7.

Hair Tresses Dipped in 1% Active Dispersons, Combed, Drained, and Dried with No Rinsing

| 1% Active Silicone Material Tested | Wet Combing | Hold of Dried Tress | Dry Combing | Texture vs. Control | Total Cumulative Score |
|---|---|---|---|---|---|
| Example 7 in water | 3.0 | 1.0 | 3.0 | 3.0 | 10 |
| Example 9 in water | 3.0 | 1.0 | 3.5 | 4.0 | 11.5 |
| Example 10 in water | 4.0 | 1.0 | 4.0 | 4.0 | 13 |
| $H_2O$ Blank | 0 | 0 | 0 | 0 | 0 |

While the best performance of the water-based systems is exhibited by the preparation containing the phospholipid composition of example 10, formulations containing the phospholipid compositions of examples 7 and 9 exhibit advantageous hair treating characteristics.

EXAMPLE 13

The tissue paper softening of the silicone-containing phospholipid composition of example 7 is evaluated in this example.
Procedure:
1. 1% by weight active silicone solution/dispersion is prepared in deionized water and adjusted with lactic acid to the 4–6 pH range.
2. Evaluation is conducted using "8"×9" paper tissues weighing approximately 1.5 grams each. The lower half of each tissue is dipped briefly into the 1% active silicone solution being tested, then the tissues are withdrawn, allowed to drain, dried and equilibrated for several hours at ambient temperature and humidity. A deionized water blank is included in the test regimen.
3. Treated tissues are evaluated (undipped versus dipped portions) and ranked for softness by a small R&D expert panel. Numerical softness rankings were assigned as follows:
0=Poor/harsh textures
1=Fair
2=Good
3=Very Good
4=Excellent/very soft textures Paper Tissues Evaluated for Softness/Texture After Dipping in 1% Active Silicone Dispersion Followed by Draining and Drying 1% Active Silicone Material Tested Softness/Texture
Example 7 sample in water 3.5
Deionized water blank 0

The tissue softening characteristics is exhibited by the formulation prepared with the silicone-containing phospholipid composition of example 11.

EXAMPLE 14

The silicone-containing phospholipid composition of example 7 is used in this example. The compatability of the silicone-containing phospholipid composition with a shampoo containing an anionic detergent is evaluated.

Testing for Compatability of a Cationic Silicone Derivative with Anionic Shampoo To test for the compatability of the cationic silicone containing phospholipid in typical anionic shampoo systems, an all-ammonium shampoo system often used in conditioning shampoos is prepared with a 15% by weight "hole" in the formulation to allow for addition of the silicone-containing phospholipid composition to material to determine if the system would remain clear. The formula for this shampoo formulation is shown below.

All-Ammonium Shampoo with 15% "Hole"

|  | % "Active" | % "As Is" |
|---|---|---|
| $NH_4$ Lauryl Ether Sulfate Colonial ALS-HV (28%) | 13.0 | 46.4 |
| $NH_4$ Lauryl Sulfate Sipon L-22 (28%) | 7.0 | 25.0 |
| Coconut Monoethanolamide MONAMID CMA | 3.0 | 3.0 |
| Ammonium Xylene Sulfonate Witconate NXS (40%) | 2.0 | 5.0 |
| Citric Acid | Q.S to pH 6.25 | Q.S to pH 6.25 |
| "Hole" |  | 15.0 |
| Demineralized Water | Q.S | 5.6 |
|  |  | 100.0% |

It is found that the shampoo formulation remains clear even after the addition of 15% by weight "as is" (4.5% silicone active) silicone-containing phospholipid composition of example 7. The shampoo also shows a noticeable drop in viscosity and a marked conditioned feel on the skin after rinsing and drying versus the same shampoo with no silicone addition.

Although some preferred embodiments have been described, many modifications and variations may be made thereto in light of the above teachings. It is therefore to be understood that within the scope of the appended claims, the invention may be practiced otherwise than as specifically described and illustrated.

What is claimed is:

1. A silicone-containing phospholipid composition having the general formula:

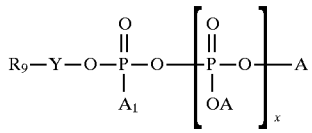

wherein:

A is selected from H, M or $R_9$—Y—;
$A_1$ is selected from H, OH, OM or $R_9$—Y—O—;
M is a cation;
x is 0 or an integer from 1 to 5;
Y is alkylene or substituted alkylene; and
$R_9$ is a silicone-containing moiety of the formula a) and the mixture thereof with an organic amidoamine moiety of the formula b), an organic tertiary amine moiety of the formula c) or mixtures of formula b) and formula c);

a) a organosilicone moiety of the formula:

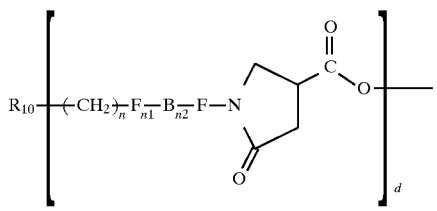

wherein:

$R_{10}$ is a silicone backbone chain to which at least one pyrrolidone containing carboxyl functional group is attached;
F, which can be the same or different, is linear or branched alkylene of 1–12 carbon atoms;
$X^-$ is an anion;
n is 0 or 2;
$n^1$ 0 or 1;
$n^2$ is 0 or 1;
B is —$NR_{11}$, sulfur (S) or oxygen (O), wherein $R_{11}$ is hydrogen or lower alkyl ($C_{1-6}$); with the proviso that when n is 0 and $n^2$ is 1, $n^1$ is 1, when n is 2 and $n^2$ is 1, $n^1$ is 0 or 1 and when n is 2 and $n^2$ is 0, $n^1$ is 0; and
d is one or greater;

b) a quaternized organic amidoamine moiety of the formula:

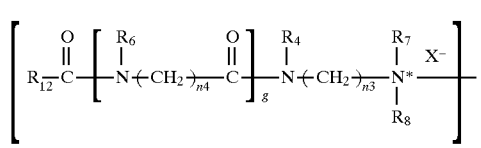

wherein:

$R_{12}$ is alkyl, alkenyl, alkoxy or hydroxyalkyl of from 5 to 21 carbon atoms each, alkaryl or aryl of up to 20 carbon atoms;
$R_6$ is hydrogen, alkyl, hydroxyalkyl or alkenyl of up to 6 carbon atoms each, cycloalkyl of up to 6 carbon atoms, or polyoxyalkylene of up to 10 carbon atoms within the oxyalkylene unit;
$R_7$ and $R_8$ which may be the same or different, are selected from alkyl, hydroxyalkyl, carboxyalkyl of up to 6 carbon atoms in each alkyl moiety, or polyoxyalkylene of up to 10 carbon atoms; or in addition $R_7$ and $R_8$ taken together with the nitrogen to which they are attached may represent an N-heterocycle;
$x^-$ is an anion;
g is 0 or 1;
$n^3$ is an integer from 2 to 12; and
$n^4$ is 1 or greater; and c) an organic quaternized tertiary amine moiety of the formula:

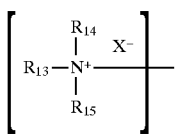

wherein:

$R_{13}$, $R_{14}$ and $R_{15}$ are the same or different and are alkyl, substituted alkyl, alkylaryl or alkenyl groups of up to 16 carbon atoms with the proviso that the total carbon atoms in $R_{13}+R_{14}+R_{15}$ is between 10 and 24;

with the proviso that at least 5 equivalent weight percent of the total equivalent weight of organosilicone and amine moieties of the phospholipid composition is an organosilicone moiety.

2. The silicone-containing phospholipid composition as claimed in claim 1, wherein $R_{10}$ is a polysiloxane backbone chain to which at least one pyrrolidone containing carboxyl functional group can be attached, said polysiloxane backbone chain having the formula:

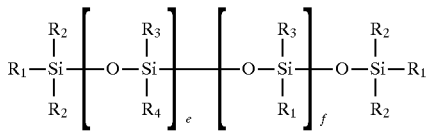

wherein:

$R_1$ can be the same or different and is selected from $R_2$, a primary amine or a pyrrolidone containing carboxyl functional group; with the proviso that at least one of $R_1$ is a pyrrolidone-containing functional group;
$R_2$ can be the same or different and is selected from alkyl, aryl, alkenyl or alkynyl;
$R_3$ and $R_4$, which may be the same or different are selected from alkyl, aryl, capped or uncapped polyoxyalkylene, alkaryl, aralkylene or alkenyl;
e is an integer from 0 to 100,000;
f is an integer from 0 to 1000.

3. The silicone-containing phospholipid composition as claimed in claim 2, wherein f is 0.

4. The silicone-containing phospholipid composition as claimed in claim 2, wherein the terminal groups $R_1$ are $R_2$ and e and f are each at least 1.

5. The silicone-containing phospholipid composition as claimed in claim 1, wherein M is an alkali metal, $X^-$ is a halogen, and d is an integer from 2 to 10.

6. A cosmetic composition for the care of skin and hair comprising at least about 0.1% by weight a silicone-containing phospholipid composition have the following general formula:

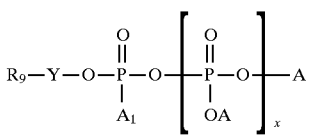

wherein:
A is selected from H, M or $R_9$—Y—;
$A_1$ is selected from H, OH, OM or $R_9$—Y—O—;
M is a cation;
x is 0 or an integer from 1 to 5;
Y is alkylene or substituted alkylene; and
$R_9$ is a silicone- containing carboxyl functional moiety of the formula a) and the mixture thereof with an organic amidoamine moiety of the formula b), an organic tertiary amine moiety of the formula c) or mixtures of the same:
a) an organosilicone moiety of the formula:

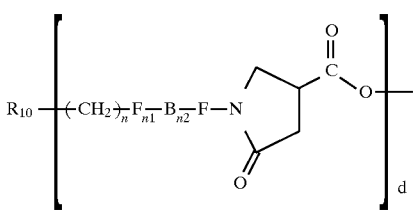

wherein:
$R_{10}$ is a silicone backbone chain to which at least one pyrrolidone containing carboxyl functional group is attached;
F which can be the same or different is linear or branched alkylene of 1–12 carbon atoms;
$X^-$ is an anion;
n is 0 or 2;
$n^1$ 0 or 1;
$n^2$ is 0 or 1;
B is —$NR_{11}$, sulfur (S) or oxygen (O), wherein $R_{11}$ is hydrogen or lower alkyl ($C_{1-6}$); with the proviso that when n is 0 and $n^2$ is 1, $n^1$ is 1, when n is 2 and $n^2$ is 1, $n^1$ is 0 or 1 and when n is 2 and $n^2$ is 0, $n^1$ is 0; and
d is one or greater;
b) a quaternized organic amidoamine moiety of the formula:

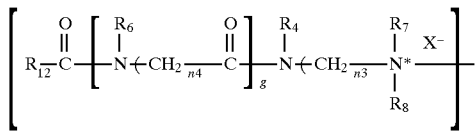

wherein:
$R_{12}$ is alkyl, alkenyl, alkoxy or hydroxyalkyl of from 5 to 21 carbon atoms each, alkaryl or aryl of up to 20 carbon atoms;
$R_6$ is hydrogen, alkyl, hydroxyalkyl or alkenyl of up to 6 carbon atoms each, cycoalkyl of up to 6 carbon atoms, or polyoxyalkylene of up to 10 carbon atoms within the oxyalkylene unit;
$R_7$ and $R_8$ which may be the same or different, are selected from alkyl, hydroxyalkyl, carboxyalkyl of up to 6 carbon atoms in each alkyl moiety, or polyoxyalkylene of up to 10 carbon atoms; or in addition $R_7$ and $R_8$ taken together with the nitrogen to which they are attached may represent an N-heterocycle;
$X^-$ is an anion;
g is 0 or 1;
$n^3$ is integer from 2 to 12; and
$n^4$ is 1 or greater; and c) an organic quaternized tertiary amine moiety of the formula:

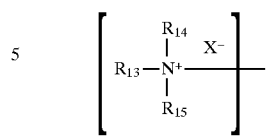

wherein:
$R_{13}$, $R_{14}$ and $R_{13}$ are the same or different and are alkyl, substituted alkyl, alkylaryl or alkenyl groups of up to 16 carbon atoms with the proviso that the total carbon atoms in $R_{13}+R_{14}+R_{15}$ is between 10 and 24;
with the proviso that at least 5 equivalent weight percent of the total equivalent weight of organosilicone and amine moieties of the phospholipid composition is a organosilicone moiety.

7. The cosmetic composition as claimed in claim 6, wherein said phospholipid compositions contains up to about 80 equivalent weight percent of a organosilicone moiety of the total equivalent weight of organosilicone and amine moieties.

8. The cosmetic composition as claimed in claim 6, wherein g in the quaternized organic amidoamine moiety formula b) is 1.

9. The silicone-containing phospholipid composition as claimed in claim 1, wherein g in the quaternized organic amidoamine moiety formula b) is 1.

10. The silicone-containing phospholipid composition as claimed in claim 1, wherein $R_2$, $R_3$ and $R_4$ are each methyl.

11. The silicone-containing phospholipid composition as claimed in claim 1, wherein Y is 2-hydroxypropylene, x is 0, and $A_1$ is OH or OM.

12. The cosmetic composition as claimed in claim 6, wherein Y is 2-hydroxypropylene, x is 0, and $A_1$ is OH or OM.

13. A method of treating hair and skin which comprises applying thereto a composition comprising from 0.1% to about 10% of a silicone-containing phospholipid composition as defined in claim :L, represented by the general formula:

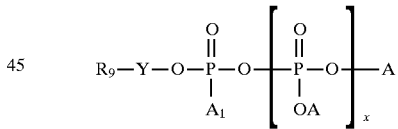

wherein:
A is selected from H, M or $R_9$—Y—;
$A_1$ is selected from H, OH, OM or $R_9$—Y—O—;
M is a cation;
x is 0 or an integer from 1 to 5;
Y is alkylene or substituted alkylene; and
$R_9$ is a silicone-containing carboxyl functional moiety of the formula a) and the mixture thereof with an organic amidoamine moiety of the formula b) an organic tertiary amine moiety of the formula c) and mixtures of the same as claimed in claim 1.

14. The silicone-containing phopsholipid composition as claimed in claim 1, wherein $R_9$ is a mixture of a silicone-containing moiety of the formula a) and a quaternized organic amidoamine moiety of the formula b).

15. The silicone-containing phospholipid composition as claimed in claim 2, wherein $R_9$ is a mixture of a silicone-containing moiety of the formula a) and a quaternized organic amidoamine moiety of the formula b).

16. A method of preparing phospholipid compositions represented by the general formula:

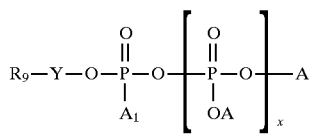

wherein:
A is selected from H, M, or R—Y;
$A_1$ is selected from H, OH, OM, or R—Y—O;
M is cation;
x is 0 or an integer from 1 to 5;
Y is alkylene or substituted alkylene; and
$R_9$ is a mixture of carboxyl functional silicone and/or tertiary amine moieties as claimed in claim 1;
which comprises reacting the combination of an organic amidoamine and/or organic tertiary amine reactant and a silicone-containing pyrrolidone-contained functional carboxyl reactant with a phosphate, phosphate or polyphosphate reactant in the equivalent weight ratios of from about 0.7 to 3.3 of total silicone amidoamine and/or tertiary amine reactants to 1 of phosphate, phosphite or polyphosphate reactant until the amine reactants are substantially completely reacted, with the proviso that at least 5 equivalent weight percent to about 80 equivalent weight percent of the total equivalent weight of silicone and amine reactants will be silicone containing, and phosphate ester reactant being of the general formula:

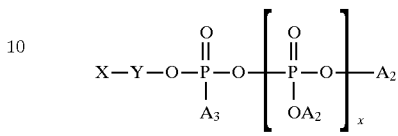

wherein:
$A_2$ is selected from H, M, X—Y;
$A_3$ is selected from H, OH, OM or X—Y—O;
Y is alkylene or substituted alkylene;
X is halogen; and
x is 0 or an integer from 1 to 5.

* * * * *